US005823772A

United States Patent [19]

Vogt

[11] Patent Number: 5,823,772

[45] Date of Patent: Oct. 20, 1998

[54] FOLDED ORTHODONTIC SPRING

[76] Inventor: William Vogt, RD 4, Box 4205, Bangor, Pa. 18013

[21] Appl. No.: 772,912

[22] Filed: Dec. 24, 1996

[51] Int. Cl.[6] .......... A61C 3/00

[52] U.S. Cl. .......... 433/21; 433/18

[58] Field of Search .......... 433/7, 18, 19, 433/20, 21

[56] References Cited

U.S. PATENT DOCUMENTS

| | | | |
|---|---|---|---|
| 4,197,643 | 4/1980 | Burstone et al. | 433/20 |
| 4,976,614 | 12/1990 | Tepper | 433/21 X |
| 5,167,499 | 12/1992 | Arndt et al. . | |
| 5,312,247 | 5/1994 | Sachdeva et al. . | |
| 5,314,331 | 5/1994 | Brosius et al. | 433/21 |
| 5,399,087 | 3/1995 | Arndt | 433/20 X |
| 5,429,501 | 7/1995 | Farzin-Nia et al. | 433/21 |

*Primary Examiner*—Nicholas D. Lucchesi
*Attorney, Agent, or Firm*—Gregory J. Gore

[57] ABSTRACT

An orthodontic spring is comprised of a wave spring made of shape memory alloy that consists of a wire tightly looped, once or many times back on itself, side-to-side in figure "8"fashion. After winding, the spring is heat treated into this position. In its relaxed state, the bends of the spring form peaks and valleys which lie in parallel planes at an angle to the line of force between attachment loops at opposite end points of the spring. Portions of the wire between successive peaks and valleys overlap other portions between other peaks and valleys when the wire is relaxed. When extended, the elements of the spring lie in a longitudinal plane along its line of force. The spring is particularly suited to attachment between closely spaced points, such as brackets affixed to adjacent teeth.

13 Claims, 1 Drawing Sheet

10
13
11
12

FOLDED ORTHODONTIC SPRING

FIELD OF THE INVENTION

This invention relates to a resilient device for aiding in the alignment of teeth through the application of tensile forces. More specifically, the invention relates to a wave-type spring made of a shape memory alloy wire, heated to a super-elastic state.

BACKGROUND AND DESCRIPTION OF PRIOR ART

Orthodontists need a device to supply tension of some sort in most of their patients. In many people, the upper row of teeth protrude substantially compared to the lower row, or the upper row is retruded behind the lower row. Also on many occasions, spaces between teeth need to be closed by moving the teeth toward each other, or space that has been closed needs to be maintained in a closed position. These types of improvements in orthodontics may be termed either protraction or retraction depending on the direction of movement. Previously, treatment involved the use of rubber bands, headgear with elastic straps, coil springs and elastic ligatures.

A disadvantage of headgear and rubber bands is that they can be removed by the patient. This makes the outcome of treatment overly dependent upon patient cooperation. Another disadvantage of headgear with elastic straps, rubber bands and elastic products is that elastics and devices dependent on them tend to fatigue with time to the point where the force level they supply becomes too low to move the teeth efficiently. This then necessitates that these products be changed or adjusted frequently. Elastic rubber bands have the further disadvantages that they have a tendency to break in the mouth, and they are many times not worn as directed.

Coil springs have the disadvantage in that they are bulky, obtrusive and uncomfortable to the patient. They catch food and are difficult to clean. Furthermore, they do not supply a constant force if made of a steel alloy, or deliver a constant force over a very limited range if they are made of a memory alloy that has super-elastic properties. They also can easily be overstretched, in which case they become deformed and deliver a much reduced force.

The closest prior art of which the applicant is aware is U.S. Pat. 5,312,247 issued to Sachdeva et al on May 17, 1994. This reference discloses the use of a shape-memory nickel-titanium alloy utilized as a transpalatal spring for expanding or contracting the dental arch. The document discloses a wave-type spring having alternating bends which lie along the natural curvature of the patient's palate orthogonal to the direction of the bends and is therefore three-dimensional.

Consequently, the need remains to provide a device for developing tensile forces that are appropriate for moving teeth in a manner consistent with what is desired for a particular treatment, and which overcomes the deficiencies with the prior art force members described above.

SUMMARY OF THE INVENTION

The invention is directed to a wave spring made of shape memory alloy that consists of a wire looped tightly once or many times, or even back on itself, side-to-side, in figure "8" fashion. After winding, the spring is heat-treated into this position. When extended, the elements of the spring lie in a longitudinal plane along its line of force. Therefore the spring, unlike a coil spring, has no loops which are perpendicular to the longitudinal axis and, hence, no coils that protrude out from the spring in any direction other than its force vector. The spring may have integral or attached end-connectors. Preferably, the spring is designed so that when it is extended, it has the property of having a very narrow profile and is thus compact and less obtrusive in the patient's mouth.

After being formed into the desired shape, the spring is heated into a super-elastic state. It can deliver a predetermined spring force when stretched within a super-elastic zone of deflection, while maintaining its tendency to return to its overlapping looped shape when it is relaxed. The spring has no active coils or helices in it, thus while it is stretched it has a tendency to become straighter and when it is unloaded its loops return. The present orthodontic device according to this invention may be employed to apply a constant predetermined force to the teeth, either to the teeth of one jaw or to the teeth between both jaws when it is connected to other orthodontic devices or to the orthodontic braces. It is particularly suited to attachment between closely-spaced points, such as attachment between adjacent teeth.

More specifically, the applicant has invented an orthodontic spring, comprising: a wire having first and second ends with the first and second attachment means located at each end. A plurality of bends extend along the wire between the attachment means and consist of sequential bends alternating in rotational direction forming waves in the wire having peaks and valleys. The peaks overlap side-to-side when the spring is relaxed in order to provide the minimum distance between the attachment means. When extended, the peaks and valleys are substantially co-planar and the attachment means lie along a longitudinal midline in the plane of the spring, of approximately equal distance between the peaks and valleys. In use, the attachment means are connected to separate orthodontic appliances attached to a patient's teeth. The attachment means may be circular loops formed in the ends of the wire, or may be separate connectors. The spring is preferably made of a super-elastic alloy wire, such as nickel titanium.

It is therefore the primary object of the present invention to provide improved orthodontic devices.

It is also an object of the present invention to provide orthodontic devices for the treatment of dental malocclusions, including protrusion or retrusion of the upper teeth relative to the lower teeth, and misalignments of the teeth relative to one another.

It is also an object of the present invention to provide orthodontic devices that can deliver a predetermined force over a long range of activation.

It is also an object of the present invention to provide orthodontic devices that supply a constant force level over a longer period of time and less susceptible to breakage.

It is also an object of the present invention to provide orthodontic devices that are unobtrusive and easy to keep clean.

Other objects, advantages and novel features of the invention will become apparent from the following detailed description of the invention when considered in conjunction with the accompanying drawings.

DESCRIPTION OF THE PREFERRED EMBODIMENT

Figure 1:
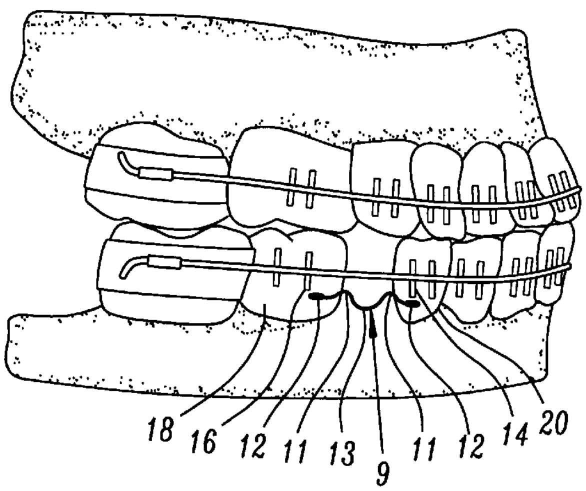
FIG. 1 is a front view of the present invention illustrated attached to intra-arch orthodontic brackets.

FIG. 1 is a illustration of the upper and lower jaws of an orthodontic patient. The spring 9 of the present invention is shown attached between brackets 14 and 16 which are affixed to teeth 18 and 20. In this figure, the wave spring 9 of the present invention is shown in its extended state applying a tensile force between appliances 14 and 16 through attachment means 10 and 12. A resilient force is provided by the deflection of the wire material at bends 11 and 13 which are located between the attachment points. Arcuate bends 11 appear uppermost along the length of the wire as peaks, and reverse-direction arcuate bend 13 appears at the lowermost point along the spring as a valley.

Figure 2:
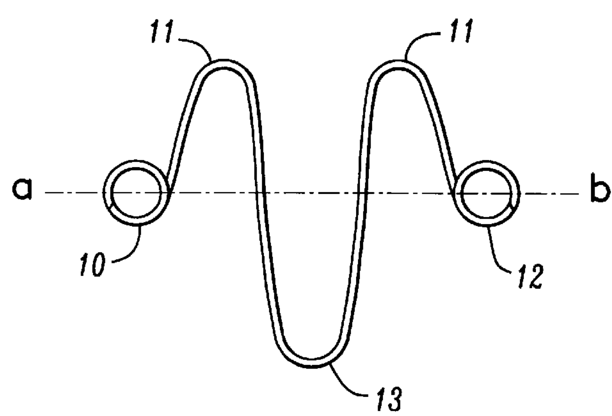
FIG. 2 is a front elevational view of the present invention shown in its extended state.

FIG. 2 shows the present invention in isolation in its extended state. In this embodiment, the spring is shown having only three bends represented by two peaks 11 and one valley 13, and the attachment loops 10 and 12 lie along midline a–b. This spring is shown in its relaxed state in FIG. 3 in which peaks 11 are shown to overlap with arcuate bends that exceed 180-degrees such that the loops are overlapped so that adjacent peaks 11 and valley bend 13 form a figure "8". This permits attachment loops 10 and 12 to be located very close together.

Figure 3:
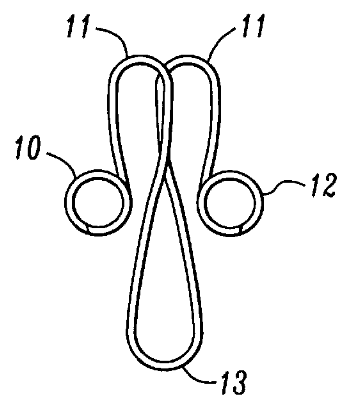
FIG. 3 is a front elevational view of the present invention in its relaxed state.
Figure 4:
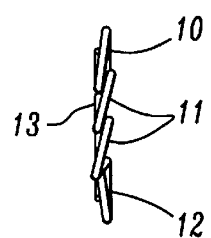
FIG. 4 is top plan view of the present invention in its relaxed state.

Referring now to FIG. 4, a top plan view of the spring of the present invention in its relaxed state as shown in FIG. 3 is depicted. It can readily be seen from this view that the overlapping of bends 11 and 13 permit attachment means 10 and 12 to have a minimal separation at rest. This provides the possibility of utilizing this spring between points which are very close, such as attachment between adjacent teeth. This is not possible with coil springs. It should be understood that additional bends may be added to create a longer spring, while maintaining a line of force between the attachment points through the center of the spring.

Figure 5:
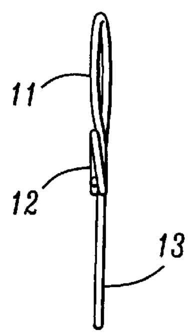
FIG. 5 is a side elevational view taken from FIG. 2.

Finally, referring to FIG. 5, a right-side view of the spring in its extended state as shown in FIG. 2 is depicted. It can be seen from this view that in use, the spring of the present invention provides a very narrow longitudinal profile and, hence, occupies very little volume in the patient's mouth.

It should be understood that the above description discloses specific embodiments of the present invention and are for purposes of illustration only. There may be other modifications and changes obvious to those of ordinary skill in the art that fall within the scope of the present invention which should be limited only by the following claims and their legal equivalents.

What is claimed is:

1. An orthodontic extension spring, comprising:

a wire having first and second ends movable between relaxed and extended positions;

first attachment means located at said first end;

a plurality of bends along said wire extending from said first attachment means, said bends sequentially alternating in rotational direction forming a plurality of waves in said wire wherein peaks and valleys lie substantially in a single plane when said wire is extended; and second attachment means located at said second end directly after said bends, wherein said portion of the wire including successive bend form a figure "8".

2. The spring of claim 1, wherein said waves in said wire overlap, side-to-side, when said spring is relaxed.

3. The spring of claim 2, wherein said first and second attachment means lie along a longitudinal midline which extends in the plane of said spring approximately equidistant between said peaks and said valleys.

4. The spring of claim 3, wherein said first and second attachment means are connected to separate orthodontic brackets which are in-turn are adapted to be attached to human teeth.

5. The spring of claim 4, further described in that said spring is composed of a metallic alloy wire.

6. The spring of claim 5, wherein said spring is composed of super-elastic nickel titanium.

7. The spring of claim 4, further described in that said human teeth are located along the same dental arch.

8. The spring of claim 7, wherein said teeth are adjacent.

9. The spring of claim 3, further described as being a wholly integral length of wire.

10. The spring of claim 9, wherein said attachment means are circular loops formed on the ends of said wire.

11. An orthodontic extension spring, comprising:

a wire having first and second ends movable between relaxed and extended positions;

first attachment means located at said first end;

a plurality of bends along said wire extending from said first attachment means, said bends sequentially alternating in rotational direction forming a plurality of waves in said wire wherein peaks and valleys of said waves lie substantially in a single plane when said wire is extended;

second attachment means located at said second end directly after said bends; and said wire being formed such that portions of said wire adjacent to said peaks lie in parallel planes at an angle to a line of force between said first and said second attachment means when said spring is relaxed.

12. The orthodontic spring of claim 11, wherein said first and second attachment means are adapted to be affixed to adjacent teeth.

13. An orthodontic extension spring, comprising:

a wire having first and second ends movable between relaxed and extended positions;

first attachment means located at said first end;

a plurality of bends along said wire extending from said first attachment means, said bends sequentially alternating in rotational direction forming a plurality of waves in said wire wherein peaks and valleys of said waves lie substantially in a single plane when said wire is extended;

second attachment means located at said second end directly after said bends; and said wire being formed such that portions between successive peaks and valleys overlap other portions between other peaks and valleys when the wire is relaxed.

* * * * *